United States Patent
Inman et al.

(10) Patent No.: US 10,799,152 B2
(45) Date of Patent: Oct. 13, 2020

(54) SYSTEM AND METHOD FOR MOTION DETECTION AND ACCOUNTING

(71) Applicant: Medtronic Xomed, Inc., Jacksonville, FL (US)

(72) Inventors: Dana Michael Inman, Jacksonville, FL (US); Kevin L. McFarlin, St. Johns, FL (US); Wenjeng Li, St. Johns, FL (US)

(73) Assignee: Medtronic Xomed, Inc., Jacksonville, FL (US)

( * ) Notice: Subject to any disclaimer, the term of this patent is extended or adjusted under 35 U.S.C. 154(b) by 395 days.

(21) Appl. No.: 15/234,530

(22) Filed: Aug. 11, 2016

(65) Prior Publication Data

US 2018/0042524 A1    Feb. 15, 2018

(51) Int. Cl.
*A61B 5/11*    (2006.01)
*A61B 5/00*    (2006.01)
(Continued)

(52) U.S. Cl.
CPC .......... *A61B 5/1104* (2013.01); *A61B 5/0488* (2013.01); *A61B 5/1107* (2013.01);
(Continued)

(58) Field of Classification Search
CPC .............. A61M 16/04; A61M 16/0411; A61M 16/0434; A61M 16/0463; A61M 2205/0294; A61M 2205/3306; A61M 2205/332; A61M 2205/3344; A61M 2210/065; A61M 2230/08; A61N 1/0517; A61N 1/0519; A61N 1/0556; A61N 1/36053; A61N 1/36114; A61N 1/36003;
(Continued)

(56) References Cited

U.S. PATENT DOCUMENTS 5,024,228 A * 6/1991 Goldstone ............ A61B 5/0421
600/380
8,594,805 B2 * 11/2013 Hincapie Ordonez .....................
A61B 5/4035
607/62

(Continued)

FOREIGN PATENT DOCUMENTS

AU    2015200049 A1    2/2015
WO    2016064870 A1    4/2016

OTHER PUBLICATIONS

Internet Archive, Mouser Electronics, "MEMS Enable Medical Innovation" Apr. 28, 2015. Retrieved from <https://web.archive.org/web/20150428143519/https://www.mouser.com/applications/mems-enable-medical/> on Sep. 10, 2018.*
(Continued)

*Primary Examiner* — David J. McCrosky
(74) *Attorney, Agent, or Firm* — Harness Dickey

(57) ABSTRACT

A stimulation electrode assembly configured to be positioned relative to a patient for an operative procedure is disclosed. An evoked stimulation response may be sensed by a sensor near a portion of a subject. The evoked response may be sensed by an electrode and determined with a monitoring system. The evoked response may additionally and/or alternatively be sensed with a motion sensor. A position sensor may be provided to measure or determine whether the sensor has moved during a procedure.

11 Claims, 4 Drawing Sheets

(51) Int. Cl.
*A61M 16/04* (2006.01)
*A61B 5/0488* (2006.01)
(52) U.S. Cl.
CPC .......... *A61B 5/4041* (2013.01); *A61B 5/4893* (2013.01); *A61B 5/687* (2013.01); *A61M 16/04* (2013.01); *A61B 5/6847* (2013.01); *A61B 5/6852* (2013.01); *A61B 2562/0219* (2013.01); *A61M 2205/054* (2013.01)
(58) Field of Classification Search
CPC .............. A61N 1/36007; A61N 1/3627; A61N 1/36139; A61N 1/3601; A61B 5/0488; A61B 5/0492; A61B 1/2673; A61B 2562/0209; A61B 2562/0215; A61B 5/04012; A61B 5/0421; A61B 5/04886; A61B 5/062; A61B 5/064; A61B 5/065; A61B 5/4035
See application file for complete search history.

(56) References Cited

U.S. PATENT DOCUMENTS

| | | |
|---|---|---|
| 9,037,226 B2 | 5/2015 | Hacker et al. |
| 2013/0053926 A1 | 2/2013 | Hincapie Ordonez et al. |
| 2014/0014869 A1 | 1/2014 | Fink et al. |
| 2014/0180138 A1 | 6/2014 | Freeman et al. |
| 2014/0363801 A1* | 12/2014 | Samosky ................. G09B 5/02 434/267 |
| 2015/0088029 A1* | 3/2015 | Wybo .................. A61B 5/1107 600/554 |
| 2016/0038072 A1 | 2/2016 | Brown et al. |
| 2016/0038073 A1 | 2/2016 | Brown et al. |

OTHER PUBLICATIONS

International Search Report and Written Opinion dated Nov. 14, 2017 in corresponding International Application No. PCT/US2017/046312.

Schneider et al. "Continuous intraoperative vagus nerve stimulation for identification of imminent recurrent laryngeal nerve injury: Continuous IONM for Thyroid Surgery", Head and Neck, vol. 35, No. 11, Nov. 1, 2013, pp. 1591-1598, XP055421596, US ISSN: 1043-3074, DOI 10.1002/hed.23187.

International Preliminary Report on Patentability dated Feb. 21, 2019 in corresponding International Application No. PCT/US2017/046312.

* cited by examiner

SYSTEM AND METHOD FOR MOTION DETECTION AND ACCOUNTING

FIELD

The present disclosure relates to activity monitoring, and particularly to motion monitoring devices and methods.

BACKGROUND

This section provides background information related to the present disclosure which is not necessarily prior art.

During various procedures, such as various throat procedures or other procedures occurring near and/or adjacent to nerve fiber, a determination of nerve integrity or stimulation may be selected. Determining nerve integrity may include ensuring or monitoring stimulation activity along a nerve. This may include transmission of or receiving an induced signal on a nerve. In performing such integrity monitoring, an electrode or electrode containing element is connected to a nerve or nerve fiber to monitor or stimulate the nerve fiber. Monitoring of an evoked signal at a single time or over a period of time can assist in determining integrity and continuity of a nerve. Various monitoring systems include the NIM-Response® 3.0 sold by Medtronic, Inc. having a place of business in Minneapolis, Minn. The monitor systems can include or be operated with an electrode including an APS® electrode that allows for automatic and periodic stimulation of a nerve that may be monitored by the system.

SUMMARY

This section provides a general summary of the disclosure, and is not a comprehensive disclosure of its full scope or all of its features.

A system to provide stimulation to selected nerve bundles or paths is disclosed that includes a selected cuff or other connector of electrodes to connect to nerves or nerve bundles. The connectors may be wired or wireless. A wireless stimulator assembly can be positioned adjacent to or near a nerve for stimulating the nerve and/or detecting a stimulation of the nerve. The connector may include electrodes that may contact the nerve when connected. The connector may include an active fixation that positively connects or surrounds at least a portion of the nerve bundle. In the alternative, electrodes may be placed to contact the nerve, but not surround the nerve.

A monitoring system may include a processor that may be an application specific processor or can be a general purpose processor that is able to execute instructions stored in a memory. The memory may be a physical memory that is incorporated into the monitoring system or accessed via a network. The instructions are executed by the processor to analyze a received signal, such as an electromyography (EMG), in a muscle to assist in determining integrity of a nerve over time. The monitoring system may further include a display device, audio output, or other output for a user to view the results of the monitoring.

Signals received may be with a monitoring electrode that is positioned at a location away from the stimulating or transmission electrode. The monitoring electrode may, for example, be on an endotracheal tube. The tube may be positioned in a tracheal passage of a subject, such as a human patient during a selected procedure. The monitoring electrode positioned on the tube may sense a response, such as an EMG response in a muscle, due to stimulation of a selected nerve by a transmitting electrode and a signal may be displayed on the monitoring system. The signal at the monitoring electrode may be sensitive to motion and/or position change. A position monitoring or movement monitoring sensor may be provided with the tube.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
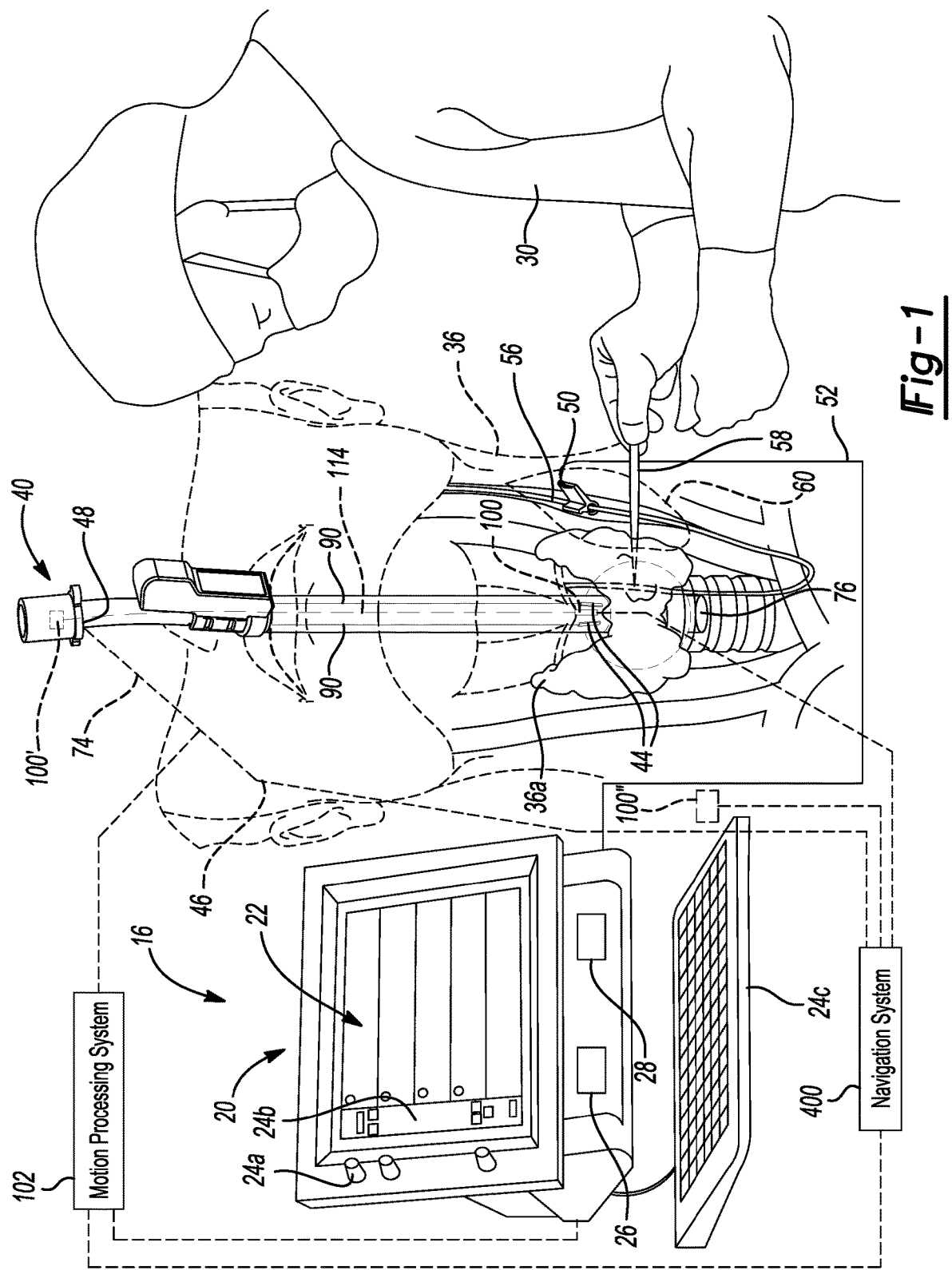
FIG. 1 is an environmental view of a monitoring system and an electrode assembly.

With initial reference to FIG. 1 a monitoring system 16, such as a NIM® nerve integrity monitoring system may include a monitor assembly 20 that has a display screen or device 22 and one or more input devices. The input device may include one or more systems or structures to input commands of information such as knobs 24a, a touch screen 24b, a keyboard 24c, or other appropriate input devices. Input devices may also include audio or other tactile input devices, including electronic or physical input devices.

The monitor assembly 20 may further include a processor 26 and a memory 28. It is understood that the processor 26 may access the memory 28 to execute instructions stored on or access other data on the memory 28. The memory 28 may include a physical memory, such as a spinning hard disk drive, solid state memory, or other appropriate types of memory. Further, the memory 28 may not be incorporated into the monitor assembly 20, but may be accessed by processor 26, such as via communications network. The processor 26 may be a general purpose processor that is operable to execute instructions for generating a selected output, as discussed further herein. The processor 26 may further include onboard memory. Moreover, the processor 26 may include a specific purpose processor such as an application specific integrated circuit (ASIC). Accordingly, the processor 26 may execute instructions stored on memory 28, which may be a non-transitory memory, to provide an output for display on the display device 22. A user 30 may then view the display device 22 for selected purposes, as discussed further herein.

Connected with the monitor assembly 20, may be one or more stimulation or monitoring assemblies. For example, in various procedures such as a thyroidectomy or other thyroid surgeries, monitoring of a recurrent laryngeal nerve (RLN), a vagus nerve, or other appropriate nerve, in a patient 36 may be selected. Monitoring of the RLN may include a nerve monitoring endotracheal tube assembly 40 that may have one or more monitoring portions, including one or more conductive electrode contacts 44. The electrode contacts 44 may be in contact with selected portions of the patient 36, such as a human patient. The electrode contacts 44 may be connected to the monitor 20 via a connection, such as an optional wired connection (also referred to as a line or hardline) 46 or wireless connection including a wireless transmitter 48. It is understood, however, regardless of the connection to the monitor 20, a transmitted signal from the electrode contacts 44 may be made to the monitor assembly 20. An exemplary endotracheal tube may include a NIM Trivantage® monitoring tube sold by Medtronic, Inc. Exemplary endotracheal tubes may further include those disclosed in U.S. patent application Ser. No. 14/455,258, now U.S. Pat. App. Pub. No. 2016/0038072, incorporated herein by reference. It is understood, however, that the tube 40 may include portions in addition to those currently available or different from those currently available on the NIM Trivantage® monitoring tube and those discussed above.

In addition, other instruments may be connected to the monitor 20, such as electrode assemblies, including an electrode that may send or receive periodic stimulation pulses, including, according to various embodiments, a connected electrode assembly 50, as illustrated in FIG. 1. The connected electrode assembly 50 may be connected with a physical connection, such as a wire 52 to the monitor 20. The connected electrode assembly 50 may also, or alternatively, be connected via a wireless transmission or otherwise provide a stimulation to a nerve 56. Other instruments may also be connected with the monitor 20 that may be used to send or receive stimulation signals to the patient to assist in determining whether nerve damage or other tissue damage has occurred or could occur. An instrument 58 (e.g. a scalpel, forceps, etc.) may be manipulated by the user 30, such as a human surgeon, and need not be directly connected to the monitor 20. The instrument 58 may have a stimulation signal that is transmitted to evoke a nerve action potential that may be received through the contacts 44 of the tube 40. The instrument 58 may be used to dissect and/or resect tissue within the patient and through an incision 60.

The operation of the monitoring system and the use of the monitoring system 16 may be similar to the NIM® monitoring system sold by Medtronic, Inc., including the NIM-Response® 3.0 nerve monitoring system. In operation, the electrode assembly 50 may be connected with the nerve 56 and a signal may be transmitted along the connection 52 from the monitor system 20 through the electrode 50 to the nerve 56. The electrode contacts 44 may then receive an EMG signal, such as in a muscle, that is evoked by the stimulation of the electrode 50.

Figure 2:
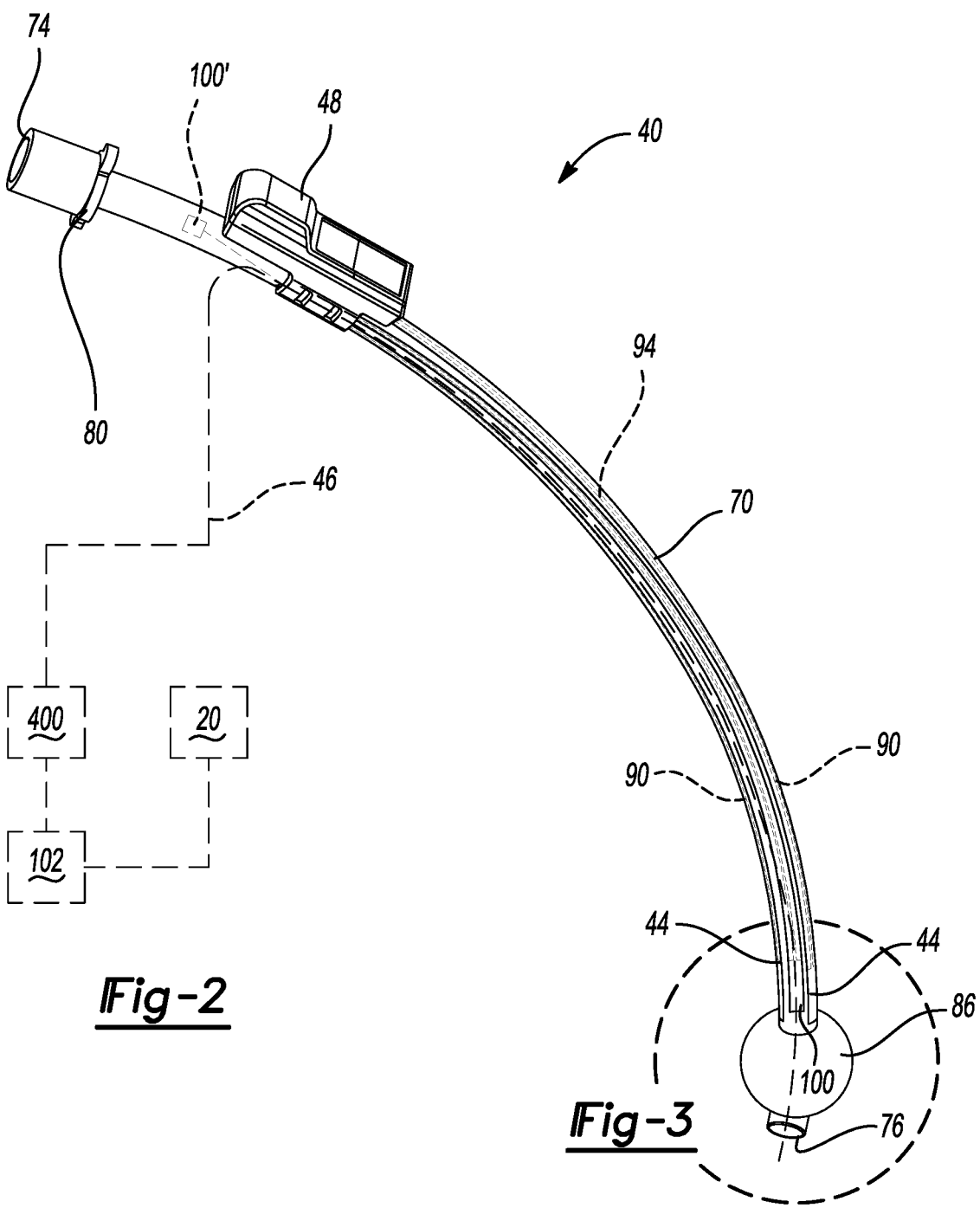
FIG. 2 is a perspective view of an electrode assembly, according to various embodiments, with an endotracheal tube.
Figure 3:
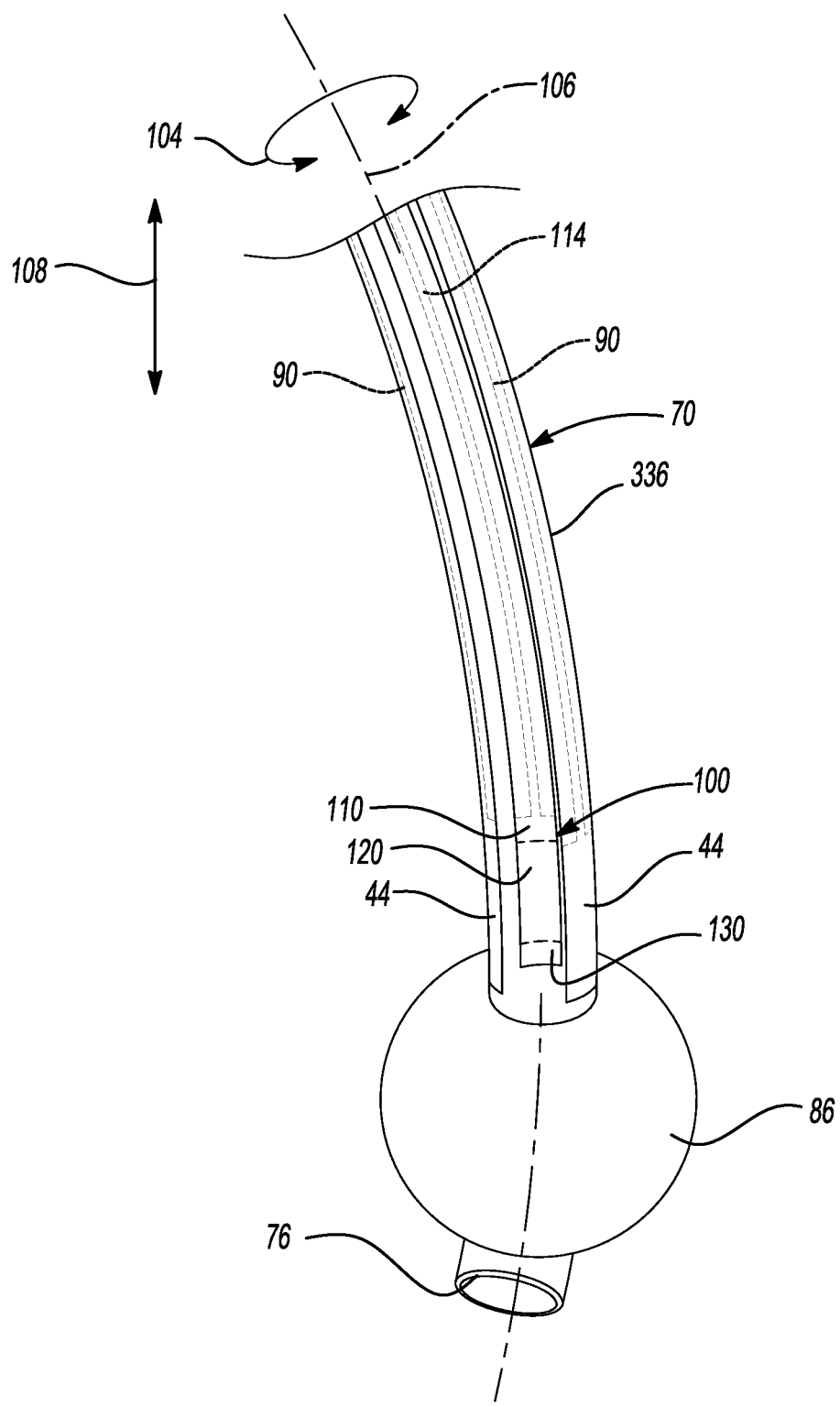
FIG. 3 is a detail view of a portion of the endotracheal tube of FIG. 2.

The tube 40, as discussed briefly above, is illustrated in detail in FIGS. 2 and 3. The tube 40 may be an EMG endotracheal tube assembly 40 and a corresponding housing 70. The EMG endotracheal tube assembly 40 may include the housing 70 and an electronic assembly including a wireless transmission assembly 48 and/or the wired connection 46. The tube assembly 40 includes a tube distal (first) end 74 and a proximal (second) end 76. The distal end 74 is connected to a connector 80, which may be connected to a pump for supplying a selected material such as a gas and/or a fluid to a patient via the tube 40. The tube 40 may be inserted in a throat of the patient 36 and the gas and/or fluid may be supplied to, for example, lungs of the patient 36. The proximal end 76 includes an inflatable portion 86 (shown in an inflated state), which may be used to seal off, for example, a trachea, to prevent any other fluid or substance from passing around the inflated portion 86 and entering the lungs.

The tube assembly 40 includes the contacts 44. The contacts 44 may be in electrical connection with electrodes 90 formed on or in the housing 70. The contacts 44 and/or the electrodes 90 may be painted or printed on the EMG tube housing 70. For example, a conductive paint or ink may be applied to the tube housing 70, or a portion thereof to form the conductive portions. Further, the electrodes and transmission portions may include traces that are formed on flexible printed circuit boards and applied to the housing 70. A coating or protective layer may also be provided over the painted portions, while allowing the contacts 44 to be exposed to an external environment. In another embodiment, the electrodes 90 and/or the contacts 44 are printed on the EMG tube housing 70 and/or are implemented as a portion of a flexible printed circuit board (PCB).

The electrodes 90 may extend from the contacts 44 to the connection portion, including the wireless transmitter 48 and/or the wired connection 46. The electrodes 90 may extend in parallel along the tube housing 70 and are separated as to not be in contact with each other. One or more insulation layers 94 may be applied over the electrodes 90 to prevent external electrical contact with the electrodes 90. Each of the insulation layers 94 may cover one or more of the electrodes 90 and may not wrap fully around the tube housing 70. The insulation layers 94 may be nonconductive stamps formed of nonconductive material (e.g., rubber).

As discussed above, the tube assembly 40 may be used with the monitoring assembly 20 to monitor an electrical activity signal in the patient 36. The stimulation being sensed through the contacts 44 may be provided through the electrode assembly 50 in connection with the monitor assembly 20. As discussed above, the NIM® stimulation and monitoring system sold by Medtronic, Inc. may be provided to sense at or stimulate the nerve 56, or any selected nerve, at a selected rate or interval and sense or detect the stimulation of the nerve 56. Upon sensing the stimulation from the nerve (including, for example, an EMG response of a muscle and/or electrical activity related thereto) the monitoring system 20 may monitor the EMG signal after determining a baseline and to determine the baseline. Further, the user or other appropriate individual may observe the monitoring system 20, such as the display 22, to ensure integrity of nerves during a surgical procedure. Procedures may include a throat or thyroid removal procedure, as discussed above.

The multiple contacts 44 can be provided around the tube assembly 40 for various purposes. In various embodiments, the multiple electrodes and/or contacts therefore may be used for differentiating between left and right nerves, differentiating between different nerves and nerve branches, compensating for users placing the tube contacts in a variety of depths and/or axial positions relative to the anatomy. The multiple electrodes may be placed axially along the tube to allow for measurements at a distance from a selected location as well. Referential recording electrodes may also be placed a distance from other recording electrodes to minimize noise and interference. Upon movement of the contacts 44 relative to the patient 36 (including internal tissue, such as muscle 36a that may include vocal fold in a human larynx) the signal to the monitoring system 20 may change. Change of the signal to the monitoring system 20 may be interpreted or possibly interpreted as an injury to the nerve 56. The system 20, upon determining a change or sensing a change in the received stimulation, may provide an indication to the user 30 that an injury has occurred and that the procedure should be stopped, if the signal to the monitoring system 20, however, changes only due to movement, whether intentional or unintentional, of the tube assembly 40 then no injury has occurred.

Accordingly, a movement or motion detection system including one or more move or motion sensors 100, which may also be referred to as a motion sensing portion, may be provided on the tube assembly 40. The motion sensor 100 may be interconnected with the wireless module 48 or the conductive connection (e.g. a wired connection) 46 to the monitoring system 20. Motion detected by the one or more motion sensor 100 can assist in determining whether the tube assembly 40 has moved relative to the patient 36 and assist in determining whether a change in signal sensed by the contacts 44 is due to movement of the tube assembly 40 or due to a cut or injury to the nerve 56. A signal from the motion sensor 100 may be transmitted to a motion processing system 102. The signal may be processed with the motion processing system 102 to determine type, speed, amount, etc. of motion. The processed motion signal may then be transmitted to the processor 26. It is understood, however, that the motion processing system may be incorporated into the monitoring system 20. For example, the processor 26 may execute specific instructions stored on the memory system 28 to operate at the motion processing system 102 to determine motion of the motion system 100.

With additional reference to FIG. 3 the motion sensor 100 can be provided near or at the proximal end 76 of the tube assembly 40. In various embodiments, the motion sensor 100 is at or near the location of the contacts 44. For example, the motion sensor 100 may be provided substantially adjacent to the contacts 44. In providing the motion sensor 100 near or adjacent to the contacts 44, movement of the contacts 44 can be substantially directly determined due to sensed or measured motion of the motion sensor 100. One skilled in the art, however, will understand, that the motion sensor 100 may be provided at the distal end or near the distal end 74. Optionally, the assembly 40 may include the motion sensor 100 and a second motion sensor 100'. The second motion sensor 100' may be spaced apart from the first motion sensor 100, such as being placed at the distal end 76. The second motion sensor 100' may also be provided with communication to one or more of the wireless transmission assembly 48 or through the line 46 to transmit to the motion processing system 102 and/or the monitor 20. Thus, it is further understood, that the assembly 40 may include one or more of the motion sensors 100, and the discussion herein of the motion sensor 100 is merely exemplary.

The motion sensor 100 may be used to measure an amount or type of motion and determine motion of the contacts 44 and/or the tube assembly 40. The motion of the tube assembly 40 and/or the contacts 44 may be determined in absolute measurement and/or relative to the patient 36. For example, the motion sensor 100 can be used to determine rotational or angular movement, such as in the direction of arrow 104 around a central or longitudinal axis 106 of the tube assembly 40. Further, the motion sensor 100 can be used to determine axial motion such as in the direction of double headed arrow 108 along the axis 106 of the tube assembly 40. Therefore, the motion sensor 100 can be provided to determine one or more dimensional movement of the tube assembly 40 including the contacts 44. As discussed herein, the motion sensor 100 may also be operated to sense or determine an evoked response to the stimulation alone or in combination with the contacts 44. An evoked response may generally include a movement of the muscle, thus motion on the tube assembly due to a contracting muscle may be sensed and/or measured with the motion sensor 100.

The motion sensor 100 can include selected motion sensors such as an accelerometer or accelerometer portion 110. The motion sensor 100 can include one or more types of motion sensors, as discussed further herein. In various embodiments, the motion sensor 100 may include only the accelerometer 110.

The accelerometer portion 110 can include an appropriately sized accelerometer that may be positioned on the housing 70 of the tube assembly 40. Exemplary accelerometers include microelectrode-mechanical systems (MEMS). It is understood that other appropriate types of accelerometers may also be used such as thermal MEMS or other selected accelerometer devices. Generally, the accelerometer portion 110 may be provided at a selected dimension such as several microns in thickness to be provided in or on top of the housing 70. The accelerometer portion 110 may include, for example, the XTRINSIC® MA8491Q accelerometer sold by NXP Semiconductors Netherlands B.V., having a place of business in the Netherlands.

The accelerometer portion 110 may be fixed to the housing at a selected position relative to the contacts 44. For example, the accelerometer portion 110 may be adhered or molded to the housing 70. As discussed above, the electrodes 90 may be covered with the coating 94, and the coating 94 may fix or assist in fixing the position of the accelerometer portion 110 relative to the contacts 44.

The accelerometer portion 110, and any other appropriate portions including with the motion sensor 100, may be connected to the transmission device 48 and/or the line 46 through appropriate communication lines such as a communication conduit 114. The communication line 114 can include conductive printed ink or paint or other appropriate electrode forming mechanisms, similar to the connectors or electrodes 90. The accelerometer portion 110, however, is generally provided to communicate with the monitoring assembly 20.

As is understood by one skilled in the art, the accelerometer 110 may measure acceleration in one or more axis, including two axes accelerometer or a three axes accelerometer. The accelerometer, when at rest, such as in the patient 36 during an operative procedure, will generally measure acceleration down towards the center of Earth due to gravity. Upon movement of the accelerometer 110, the accelerometer 110 may measure the change in acceleration in one or more axes due to movement of the accelerometer 110. For example, during the operative procedure the tube assembly 40 may be twisted around the axis 106 in the direction of arrow 104 and the accelerometer 110 may measure the acceleration due to movement of the tube assembly 40 around the axis 106.

As discussed above, movement of the tube assembly 40 may cause movement of the contacts 44 and therefore a change in the EMG signal at the monitoring system 20. As discussed further herein, a determined correlation between (such as occurring at the same time or close in time) a sensed or measured movement by the accelerometer 110 and a change in the EMG signal sensed by the contacts 44 may allow for a determination that injury has not occurred to the patient 36 and the procedure may continue. Thus, the monitor system 20 may determine that warning state (i.e. a selected change in the EMG signal) is a false warning.

The motion sensor 100 may include portions in addition to the accelerometer 110, as noted above, including a one or more axes gyroscope, such as a three axis gyroscope 120.

The three axis gyroscope 120 may measure a rotational movement or angular movement directly due to the included gyroscope. As noted above the accelerometer 110 may need to infer or determine motion relative to gravity. Therefore, the gyroscope 120 may be able to act as a back-up or check for the accelerometer 110 by determining angular motion directly. It is understood, however, that the gyroscope 120 may be provided alone as the motion sensor 100.

The gyroscope 120 as a part of the motion sensor 100 may be positioned near or adjacent near the contacts 44. Therefore, as discussed herein, movement of the electrodes 44 may be determined by sensing motion via the gyroscope 120 and may be transmitted as a signal along the communication line 114, as discussed above. The monitoring system 20 can then determine that motion of the gyroscope 120 has occurred and may infer that motion of the electrode contacts 44 has also occurred.

Exemplary gyroscopes can include MEMS gyroscopes that can be formed on selected substrates, including silicon substrates similar to integrated circuits or printed circuit boards. Exemplary MEMS gyroscopes can include those sold by NXP Semiconductors Netherlands B.V., to measure an angular rate. As the gyroscope may measure one or more axes of motion such as include yaw, pitch and roll. Therefore, the gyroscope 120 may be used to determine direct angular motion or acceleration of the motion sensor 100 and, therefore determine angular motion of the contacts 44. Again, as discussed herein, motion of the contacts 44 may be used to deduce a reason for a change in the signal.

The motion sensor 100 may further include magnetometers 130. A magnetometer may be used to determine magnet poles that may affect a determined movement or orientation of the motion sensor 100. Magnetometer 130 may also or alternatively be operated to determine a position of the magnetometer 130 relative to magnetic poles, such as those generated by the Earth. The magnetometer 130 may operate to determine an absolute position relative to a magnetic pole, such as of the Earth, or motion relative to a magnetic pole.

The magnetometer 130 may include small or micro-magnetometers, such as MEMS magnetometers including those manufactured and sold by NXP Semiconductors Netherlands B.V., having a place of business in the Netherlands. The magnetometer may send a signal with the communication line 114 to the monitor assembly 20 to assist in determining motion or movement of the motion sensor 100 and, therefore, the contacts 44.

The motion sensor 100 can include various components and portions, including those discussed above. In exemplary embodiments, the motion sensor 100 may include only one of the accelerometers 110, gyroscope 120, or magnetometer 130. Further, it is understood that the motion sensor 100 may include any two of the three or all three of the components discussed above. According to various embodiments, the motion sensor 100 may include a six axis motion detector including the accelerometer 110 and the magnetometer 130. It may be selected, however, that additional information may be necessary to assist in ensuring accuracy for determining motion or movement of the contacts 44, therefore all three of the components may be provided. Further, in various embodiments, only the accelerometer 110 may be provided to assist in determining motion of the contacts 44. Including the gyroscope 120 may assist in reducing the effects of magnetic interference and/or various types of acceleration, such as linear acceleration of the motion sensor 100.

Returning reference to FIGS. 1 and 2, one skilled in the art will further understood, a tracking or navigation system 400 may be used to determine position change and/or motion of the tube assembly 40 including the contacts 44. For example, the tracking system 400 may include an electromagnetic tracking system that may include a localizer that is configured to emit or receive a magnetic field. A tracking sensor may be provided as the motion sensor 100, 100', 100" that is configured to emit or receive a magnetic field. A tracking system may then determine a location (including x-y-z and orientation) of the tracking sensor based on the sensed field (either at the localizer or at the tracking device). A tracked change in location may be used to determine motion. Exemplary tracking systems include those disclosed in U.S. Pat. App. Pub. 2014/014869, incorporated herein by reference. It is further understood that various tracking systems may include optical tracking systems, sonic tracking systems, electro-potential tracking systems, etc. A tracked change in location may be transmitted to the motion processing system 102 and/or the monitoring 20.

As discussed above, the tube assembly 40 may further include the motion sensor 100' at or near a distal end of the tube assembly 40. It is also understood that the motion sensor 100' may be the only motion sensor on the tube assembly 40 and that motion of the contacts 44 may be inferred from the motion sensor 100'. The motion sensor 100' may be identical to the motion sensor 100 or different, such as including more or less components.

In further embodiments a third motion sensor 100" may be provided on the patient 36 and may be referred to as a subject motion sensing portion. Including motion sensor 100" fixed directly on the patient 36 can allow for determination of motion or movement of the patient 36 independent of the tube assembly 40 including motion sensors 100 and 100'. The third motion sensor 100" may also transmit a signal to the motion processing system 102 and/or the monitor 20, as discussed above. The determination of movement of the patient 36 can be used to assist in determining whether the tube 40 has simply moved in space or moved relative to the patient 36, such as relative to the nerve 56 and/or muscle tissue innervated by the nerve 56. This can be used to assist to determine whether an anomalous or changed received signal is due to motion of the tube 40 relative to the patient 36 causing the contacts 44 to move relative to the patient 36.

If the motion sensor 100, 100' move in a manner similar or identical to the motion sensor 100" then a change in signal may signify a possible injury. If the motion sensor 100, 100' move in a manner different (such as at a different rate or time or amount) to the motion sensor 100" then a change in signal may signify only that the contacts 44 have moved relative to the patient 36. As discussed herein, a threshold amount of difference may be used in the determination. Further, monitoring system 20 may be provided to determine the type of change and possible injury.

Accordingly, it is understood that an appropriate number of motion sensors can be provided on the tube assembly 40, such as at or adjacent to the contacts 44, and on the patient 36, that operate independent of the tube assembly 40, to assist in determining possible relative motion of the contacts 44 to the patient 36. As discussed above, movement of the contacts 44 relative to the patient 36, such that their position moves over time relative to tissue of the patient 36, may cause a change in the signal received or monitored by the monitoring assembly 20.

Figure 4:
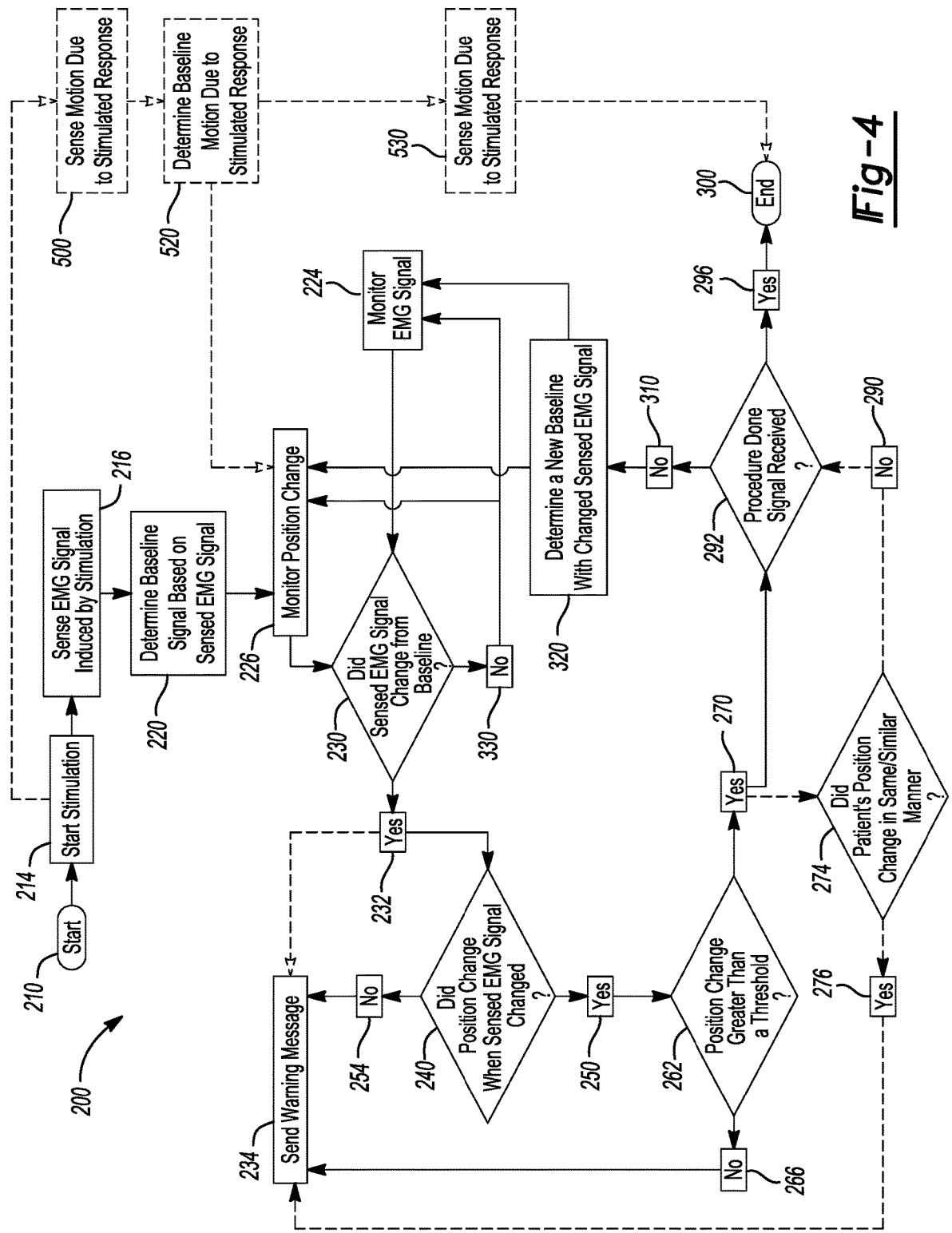
FIG. 4 is a flowchart of operation of a monitoring system, according to various embodiments.

With additional reference to FIG. 4, a flowchart 200 illustrates an exemplary operation of the monitoring system 20 which may include monitoring of an induced signal, such as with the electrode assembly 50, that is sensed at the contacts 44, of a sensing electrode, that is able to contact tissue, such as a muscle, that is stimulated due to stimulating the nerve 56. It is understood, as discussed above, that the tube 40 may be provided with the contacts 44 that are configured to sense stimulation of tissue. It is understood, however, that electrode contacts can be provided in any appropriate instrumentation or portion that may contact the patient 36 or other appropriate subject to sense a stimulation. The tube 40 is merely exemplary and provided for illustration of the current disclosure.

With specific reference to FIG. 4, therefore, the flowchart 200 may begin at START block 210. Stimulation may start in block 214, such as by operating the monitoring system 16 that include stimulating the nerve 56. As discussed above stimulation may include a periodic stimulation that may be sensed by the monitoring system 20. The periodic stimulation may have a period that accounts for various factors, such as refractory response time of the nerve 56. Nevertheless, stimulation may start in block 214.

The monitoring system 20 may then sense the EMG signal from the stimulation in block 216. As discussed above the sensed stimulation may be sensed through the contacts 44 in contact with the tissue of the patient 36 and due to the stimulation provided with the stimulation electrode 50. The sensed stimulation may cause a signal to be transmitted wirelessly via the wireless transmission system 48 or through the wired transmission system 46. The sensed signal may then be monitored and/or analyzed by the monitoring system 20.

After receiving an initial signal, such as for a selected start-up time after stimulation of the nerve 56 with the electrode 50, the monitoring system 20 may determine a baseline signal based on the sensed signal in block 220. The baseline signal determined at block 220 may be determined by the processor system 26 that is executing instructions recalled from the memory system 28. For example, the processor system 26 may determine a baseline signal including a frequency or period of stimulation, amplitude of stimulation including power or voltage, or other appropriate parameter. Regardless, the determined baseline stimulation signal may be used by the monitor system 20 to determine a baseline for later comparison.

As discussed above, the baseline signal may be determined when the nerve 56 is substantially uncompromised, such as prior to a procedure on a patient that may interfere with the nerve integrity or continuity. Accordingly, the baseline signal may be used to determine if any change from the baseline occurs, such as due to injury or the like relative to the nerve 56. Moreover, as discussed above, movement of the contacts 44 relative to tissue may also cause a change in the signal from an initial baseline. Therefore, the baseline signal may be used to assist in determining any change after an initial period in time.

The baseline signal, further, is determined at a first selected location of the contact 44. As discussed above, the sensed EMG signal may be different at different locations within the subject 36. Therefore, the contacts 44 on the tube 40 may be placed at the first location, which may be predetermined location, such as adjacent to or in contact with a specific muscle group. Movement from the first location, therefore, may cause a change in the sensed signal, including the EMG signal. If the contacts 44 move, therefore, the contacts 44 may be at a second location that is different than the first location. The second location may be rotationally, angularly, or axially displaced from the first location.

Following determination of the baseline in block 220, the sensed signal can be monitored in block 224. Further, the position or position change of the contacts 44, including the tube 40, can be monitored in block 226. The monitoring of the signal in block 224 and the position change in block 226 can both be done with the monitoring system 20. Signals may be sent to the monitoring system 20 to allow for determination of the signal due to nerve 56 stimulation after determining the baseline signal and for sensing a change in position.

At a selected period or frequency, such as every 100 milliseconds, 200 milliseconds, one second, or other appropriate frequency, a determination or measuring of whether the received signal has changed from the baseline may occur in decision block 230. A change in the signal from the baseline may include any change or a change beyond a threshold. For example, a change in the signal may include an amplitude change, a frequency change, a period change, or the like. A threshold change may include the change in the sensed signal such as a change in period of about 1% to about 10%, for example including a change of about 50 milliseconds. Therefore, if the sensed signal change includes a change in period of greater than 50 milliseconds a, determination in block 230 that a signal change has occurred will follow a YES path in block 232. It is understood that any appropriate changes in signal may also be measured and used to determine whether a change in signal has occurred such as a change in power, voltage, or the like and thresholds may include percentage changes or absolute value changes.

If the YES path 232 is followed, an optional initial warning message may be displayed or otherwise presented to the user 30 in block 234. The warning message may include any appropriate warning message such as a flashing screen, a blank screen, a verbal message, an auditory message, a visual message, or the like. Regardless the warning message at block 234 may indicate to the user 30 that the signal has changed and that a possible injury to the patient 36 has occurred.

The warning message in block 234 immediately following the YES path 232 may, however, be optional. Rather, the YES path 232 may follow to a second determination block of whether a position change was determined when the signal changed in block 240. As discussed above, the motion sensor 100 may be provided on the tube assembly 40. A position change of the tube assembly 40 may then be determined with the motion sensor 100 according to an appropriate mechanism, including the selected position sensing portions as discussed above. Therefore, determination of whether a position change occurred in block 240 may be made by the monitor system 20. A signal from the motion sensor 100 may be analyzed by the processor system 26 to determine a position change. The processor 26 may execute instructions recalled from the memory 28 to assist in determining whether the motion sensor 100 senses a change in position. The processor system 26, therefore, can also determine whether the position of the contacts 44 and/or the tube assembly 40 has changed.

The determination block 240 can follow a NO path in block 254 if no position change is determined. The NO path 254 may then follow to the send warning message in block 234. As discussed above, if a change in the sensed signal occurs and no determined position change in the motion sensor 100 is determined, then a change of the signal sensed by the contacts 44 may have changed for a reason other than movement of the contacts 44. Further possible reasons for change may be due to a change in integrity of a nerve 56 and the user 30 may be provided with a message to determine continuity of the nerve 56 and to stop the procedure, at least momentarily.

If a changed position is determined in block 240, however, a YES path 258 may be followed to a further decision block 262 including determining whether the position change was greater than a threshold. The motion sensor 100 can be used to measure a change in position of the contacts 44 or other appropriate portion of the tube assembly 40. However, a selected change, such as a small change or a slow change in position may not lead to a determination that the change in the signal determined in block 230 is due to movement of the motion sensor 100. Therefore, a selected threshold may be used to assist in eliminating or minimizing possible errors of position measurements.

Various thresholds may include a speed of change, an absolute value of change, a percent amount of change in position, or other appropriate thresholds may be used in determination block 262. In one example, if the measured change in the EMG signal is greater than plus or minus 50% from a previous measurement (e.g. when measuring once per second), but the latency of the measured signal has not changed, it may then be determined that movement of the contacts 44 due to movement of the tube 40 has caused a change in the signal. Exemplary amplitude changes may be, however, about 20% to about 80%, including about 40% to about 60%. As discussed above, this may be an automatic determination and, if selected no warning may be given in block 234, as discussed herein. In a further example, a multi-axis sensor that detects force exerted by gravity in one axis of the sensor decreases while the force exerted by gravity in another axis increases, for example by a difference of more than 30%, the processor may execute instructions to determine that the tube 40 has rotated in a known direction.

If the change is determined to be greater than a threshold in block 262, a NO path 266 may be followed to send a warning message in block 234. Again, if the change in position may not be correlated to the change in the signal then a warning message may be provided to the user 30 to determine a continuity and integrity of the nerve 56. Thus, if the amount of change is not at or greater than the threshold, the determination may be similar to no change in position being determined.

If the change is determined to be greater than the threshold in block 262, then the YES path in block 270 may be followed. Initially, in an optional embodiment, a second determination block 274 may determine whether a patient position change occurred in a same manner similar to or same as the position change of the contacts in block 240 may be made. As discussed above, an optional motion sensor 100" can be positioned on the patient 36. The motion sensor 100" allows a position of the patient 36 to also be monitored during a procedure. If a position change of the patient 36 matches the determined position change in block 240 of the motion sensor 100, then it may be inferred or determined that the patient 36 is moved during the procedure, such as turned on a side from a supine position. If the position of the patient 36 changes in a manner that is substantially the same or identical to that of the positon sensor 100 of the tube assembly 40, then a change in the signal sensed at the contacts 44 may again be determined or inferred to be a change due to something other than a movement of the contacts 44 relative to the tissue of the patient 36. This is due to the position of the contacts 44 in absolute terms relative to space outside of the patient 36 does not cause a change in the signal sensed at the contacts 44. Rather, a change in position of the contacts 44 relative to the tissue that the contacts 44 are contacting can cause a change in the sensed signal. Therefore, if it is determined that the patient had a position change in a manner that is the same as the change determined of the tube 40 in block 240, a YES path 276 may be followed to provide the warning signal in block 234. Again, the change in the sensed signal due to stimulation will have changed; however, both the position of the tube and the patient will be determined to have changed in a substantially similar manner such that the contacts 44 have not moved relative to the patient 36.

Again, optionally, if a position change of the patient determination in block 274 is made and a position of the patient changed in a manner different than the position of the tube 40 then a NO path 290 may be followed to a determination block whether a procedure done signal has been received in block 292. In this instance, the position of the patient, even if it has changed, has changed in a manner different than the position of the tube assembly 40. Therefore, it may be determined that the positon of the tube 40 relative to the patient 36 has changed and not only an absolute positon change of the tube 40.

If the position change of the tube is greater than a threshold such that the YES path 270 is followed and no optional patient position sensor is provided the YES path 270 may follow to the decision block 292 if a procedure done signal has been received. Again, if the position change of the tube assembly 40, including the contacts 44, has changed greater than a threshold a change in the sensed stimulation signal may be determined to be caused due to the movement of the tube assembly 40, including at contacts 44.

If a procedure done signal has been received then a YES path 296 may be followed to end at block 300. Ending at block 300 means ending stimulation or monitoring of the nerve 56 or other appropriate ending portions of a surgical procedure.

If a procedure done signal has not been received in block 292, a NO path 310 may be followed to determine a new baseline with a changed sense signal in block 320. As discussed above, a change sense signal may initiate a determination or check of whether the tube 40 has changed position. If it is determined that the position of the tube assembly 40 has changed it may be determined, such as with the processor system 26 executing instructions recalled from the memory 28, that the position change has caused the sensed signal change. If the position change has caused a sensed signal change then an injury to the nerve 56 may be determined to have not occurred. Therefore, if no signal to end the procedure has been received in block 292 a new baseline with the new sensed signal, different from the determined baseline signal in block 220, may be determined in block 320. After determining the new (i.e. second) baseline in block 320 monitoring of the signal in block 224 and monitoring in the position change of block 226 may continue. In this instance the procedure may then continue and monitoring of the sensing stimulation signal and the sensed position may continue and be periodically checked, as discussed above.

Further, it is understood that if no sensed changed in the stimulation is determined then a NO path 330 may be followed to continue monitoring the sensed stimulation signal in block 224 and the monitored position change signal in block 226 and these may be checked at a selected period, as discussed above. Accordingly, the monitoring system 16 can monitor a stimulation signal of the patient 36 and assist in making a determination whether the position change of the tube 40 has caused a sensed change in the stimulation signal. If a sensed position change of the tube 40 with the contacts 44 is made, then a determination may be made of whether the sensed position change has caused the change in sensed electrical stimulation.

With continuing reference to FIG. 4, and also to FIG. 1, the motion sensor 100 may be used as a monitoring portion with the monitoring system 16 to determine if a selected muscle group is being stimulated. For example, as discussed above, the muscles 36a may include or be associated with vocal folds of the subject 36. Stimulation of the nerve 56 may cause movement of the vocal folds 36a. Movement of the vocal folds 36a as an evoked response due to the stimulation of the nerve 56 may be sensed and/or measured with the motion sensor 100 (or other motion sensor associated with the tube assembly 40). Thus, the motion sensor 100 may be used to determine whether the nerve 56 is damaged or not by sensing motion of the tube assembly 40 due to movement of muscles relative to the vocal folds 36a.

In various embodiments, the motion sensor 100 (e.g. the accelerometer) can operate as the monitoring portion to detect the stimulated signal, which is the stimulation of the nerve 56, and may replace and/or augment the detection of the stimulated signal of the contacts 44, which may operate as the monitoring portion. When the nerve 56 (e.g. the recurrent laryngeal nerve and/or vagus nerve) is stimulated to evoke a response, the corresponding musculature causes vocal fold adduction and the vocal fold collides or constricts around the endotracheal tube assembly 40. These vocal fold collisions on the tube 40 induce a corresponding motion (e.g. vibration) that may be sensed by the motion detector 100 mounted on the tube assembly 40. Thus, the motion sensor 100 offers a redundant and/or alternative sensing of nerve stimulation and detecting vocal fold movement.

In various embodiments, with reference to FIG. 4, once stimulation has started in block 214 motion may be sensed due to a stimulation response in block 500. The motion sensed in block 500 may be with motion sensor 100, or any appropriate motion sensor, associated with the tube 40. The tube assembly 40 may move due to contact or collisions of selected anatomical structures, including vocal folds of the subject 36. If muscles are moved due to stimulation of the nerve 56 that caused the vocal folds to move and contact the tube 40 the motion may be sensed with the motion sensor 100. Such motion may then be inferred to relate to an evoked response of the muscles intended to be stimulated with stimulation of the nerve 56. Therefore, rather than sensing an EMG signal induced by stimulation in block 216, a motion may be sensed in block 500 to infer the same continuity of the nerve 56 to the muscles 36a.

It is understood that the motion processing system 102 may receive a motion signal from the motion sensor 100 and that the motion signal may be forwarded to the monitoring system 16. The monitoring system 16 may then execute selected instructions to determine that the evoked response at the selected muscle is occurring based on the motion signal. For example, a timing of the stimulation may be known and the timing and/or amplitude of the sensed motion may be related to the stimulation. A correlation of the time of the stimulation and the time and/or amplitude of the sensed motion may be used, therefore, to determine that the nerve 56 is uninjured. If the timing and/or amplitude (e.g. lower or no sensed motion) of the sensed motion changes a determination by the monitoring system 16 may be made that damage has occurred. As discussed herein, a warning message may then be provided to the user 30.

The monitoring system 16, therefore, upon receiving the signal from the motion processing system 102 regarding the sensed motion of the motion sensor due to movement of the vocal folds may display or present the message to the user 30, such as with the display device 22. The display device 22 may display a graph including a representation, such as a wave, representing motion. The user 30 may view the display device 22 to determine that motion is occurring, such as a selected rate, to ensure that the evoked response is still occurring. It is understood that the sensing of motion in block 500 may occur in addition to or as an alternative to the sensed EMG signal in block 216. Accordingly, it is understood that sensing motion with the motion sensor 100 to determine that the evoked response is occurring may be an alternative and/or in place of sensing EMG signal.

A determination of a baseline motion to do the stimulated response may optionally occur in block 520. The determination of the baseline motion response due to sensed motion due to the simulated response is optional, and may not be necessary. Further, it is also optional to then enter the process 200 further, as discussed above, to monitor position change in block 226. Monitoring position change in block 226 may be optional, and particularly optional when only sensing motion due to a stimulated response to determine that the evoked response is occurring. As discussed above, monitoring a position change in block 226 may occur or be selected when ensuring that movement of the contacts 44 move causes an EMG signal change. If an EMG signal is not being used to determine that the evoked response is occurring, monitoring position change in block 226 may not be selected. Therefore, determining a baseline for motion in block 520 and/or monitoring position change in block 226 when sensing and monitoring motion due to a stimulated response in block 500 may both be optional.

Regardless, a message may be provided regarding the sensed motion in block 530 with the display device 22. It is understood that other appropriate messages may also be provided to the user 30, such as an auditory or tactile message. For example, a periodic tone may be provided to the user 30 which relates to movement or sensed vibration of the tube assembly 40. The process may then end at 300 when the user 30 determines or selects to end the procedure on the subject 36.

Accordingly, the evoked response at the muscle 36a due to stimulation of the nerve 56 may be measured or determined with the motion sensor 100 on the tube assembly 40. As discussed above, vibrations of tube assembly 40 may be analyzed and used to determine that an evoked response is occurring at the selected muscle tissue due to stimulation of the nerve 56. The processor system 26 may evaluate the motion signal based upon the sensed motion by the motion sensor 100 processed by the motion processing system 102 to determine motion of the tube assembly 40. Selected signals may be provided to the user 30 such as based upon a change in a motion signal (such as an amplitude change of motion over a selected period of time) or other appropriate change in the motion signal. The sensing of the motion with the motion sensor 100, therefore, may be used in place of, or as an alternative to, sensing the EMG signal with the contacts 44 as discussed above.

This offers the advantage of a sensor (i.e. the motion sensor 100, 100', 100") that is not electrically coupled to the patient 36; thus, providing a means of sensing vocal fold movement, muscle movement, and nerve stimulation in the presence of possible electrical interference, such electrical interference may be caused by high frequency electrosurgery. Signals caused by various electrosurgery systems may cause interference with monitoring systems that attempt to sense nerve stimulation with EMG signals during the use of high frequency electrosurgical units because the voltage signals generally used to cut and cauterize tissue are much larger than the biopotentials of interest to the user 36 and/or monitored with the monitoring system 16. Another advantage of the motion sensor detecting the stimulated nerve and vocal fold movement is that the motion sensor 100 is not dependent upon placement relative to the muscle 36a (e.g. muscles relative to the vocal folds) intended to have an evoked response. The tube 40 conducts the vibrations caused by the vocal fold collisions to the motion sensor 100 regardless of the position or orientation of the motion sensor 100. It is understood, therefore, that the motion sensor 100 may include any appropriate motion sensor, including all of those discussed herein, that may be used to sense and/or measure motion of the tube 40.

It is understood that a correlation between the sensed stimulation change and the sensed position change may be made based upon various other factors such as the changes occurring at a same time or substantially similar times, such as within 10-500 microseconds of each other, including about 100 microseconds of each other. Accordingly, it will be understood that a sensed change in stimulation that occurs at a time that is outside of a selected threshold of time, such as about 100 milliseconds, may be eliminated or disregarded as a possible change due to movement of the tube assembly 40, including the contacts 44. A selected threshold of time may be selected based upon selected parameters.

An inconsequential change in position of the contacts 44 may, according to various embodiments, be disregarded when a change in a sensed stimulation signal is also measured to allow a procedure to continue without halting or interfering with the procedure to check for an injury to the nerve 56. A sensed change in the stimulation signal may provide or be used to cause a warning signal for viewing by the user 30. However, the user 30 may also be provided with a signal that a sensed change in position is determined. Therefore the user 30 may perform a less invasive determination of integrity of the nerve 56, such as monitoring the sensed stimulation signal for a selected period of time. In a selected alternative embodiment, however, the processor system 26 may execute instructions to make a determination of whether the sensed stimulation change is caused by movement of the tube assembly 40 determined by the position sensors 100, 100' and either provide a warning signal to the user 30 or only recalibrate the monitoring system 20 and determine the new baseline signal in block 320 and continue the procedure, as discussed above. Therefore, the monitoring, determining a change in the received signal based on a position change, and determining a new baseline may all be automatic without further intervention or input form the user 30.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A system to monitor a stimulation reaction in a subject, comprising:
    a motion sensing system configured to sense motion, wherein the motion sensing system includes a motion sensing portion positioned on an instrument, wherein the motion sensing portion is configured to sense a motion of at least a first portion of the subject relative to the stimulation reaction; and
    a monitoring system configured to (i) receive a motion signal regarding a possible motion of the motion sensing portion of at least the portion of the subject relative to the stimulation reaction and (ii) determine if motion is detected based on the motion signal and whether the detected motion effected the stimulation reaction that is monitored by the system.

2. The system of claim 1, further comprising:
    a stimulation electrode configured to provide a stimulation pulse at a location a distance from the first portion of the subject to evoke a response at the first portion of the subject.

3. The system of claim 2,
    wherein the instrument comprises an endotracheal tube configured to be placed in a larynx of the subject;
    wherein the motion sensing portion is fixed to the endotracheal tube.

4. The system of claim 2, wherein the monitoring system is configured to determine the evoked response in the first portion of the subject in response to the stimulation pulse based on the sensed motion with the motion sensing portion.

5. The system of claim 1, further comprising:
    a contact on the instrument in addition to the motion sensing portion configured to be in contact with at least the first portion of the subject, wherein the contact is configured to sense a response to a stimulation, wherein the stimulation caused the stimulation reaction.

6. The system of claim 5, wherein the contact includes a conductive member configured to sense an electromyography (EMG) response.

7. The system of claim 5, wherein the monitoring system includes a processor configured to execute instructions to determine a correlation between a change in the sensed response with the contact and the detected motion.

8. The system of claim 1, wherein the motion sensing portion includes at least one of an accelerometer, a gyroscope, or a magnetometer.

9. The system of claim 1, wherein the motion sensing portion includes at least two sensing portions wherein a first sensing portion of the two sensing portions is one of an accelerometer, a gyroscope, and a magnetometer and a second sensing portion of the two sensing portions is one of an accelerometer, a gyroscope, and a magnetometer.

10. The system of claim 1, wherein the motion sensing portion includes all of an accelerometer, a gyroscope, and a magnetometer.

11. The system of claim 1, further comprising:
a subject motion sensing portion, wherein the subject motion sensing portion is configured to be fixed to the subject.

* * * * *